(12) United States Patent
Mori

(10) Patent No.: US 8,292,817 B2
(45) Date of Patent: Oct. 23, 2012

(54) ULTRASONOGRAPH

(75) Inventor: Koji Mori, Ube (JP)

(73) Assignee: Yamaguchi University, Yamaguchi, Yamaguchi (JP)

(*) Notice: Subject to any disclaimer, the term of this patent is extended or adjusted under 35 U.S.C. 154(b) by 182 days.

(21) Appl. No.: 12/449,862

(22) PCT Filed: Jan. 29, 2008

(86) PCT No.: PCT/JP2008/000105
§ 371 (c)(1),
(2), (4) Date: Aug. 31, 2009

(87) PCT Pub. No.: WO2008/108054
PCT Pub. Date: Sep. 12, 2008

(65) Prior Publication Data
US 2010/0030077 A1    Feb. 4, 2010

(30) Foreign Application Priority Data
Mar. 5, 2007    (JP) .................................. 2007-53846

(51) Int. Cl.
*A61B 8/14*    (2006.01)
(52) U.S. Cl. ........ 600/459; 600/407; 600/437; 600/438; 600/442; 600/463
(58) Field of Classification Search .................. 600/407, 600/437, 438, 442, 459, 463
See application file for complete search history.

(56) References Cited

U.S. PATENT DOCUMENTS 3,683,680 A * 8/1972 Johnson et al. ................. 73/628
3,937,067 A * 2/1976 Flambard et al. ............... 73/627
4,362,059 A * 12/1982 Zwyssig .......................... 73/628
6,535,828 B1 * 3/2003 Furukawa et al. .............. 702/56

FOREIGN PATENT DOCUMENTS

| JP | 61-290942 | 12/1986 |
|----|-----------|---------|
| JP | 10-118062 | 5/1998 |
| JP | 11-316215 | 11/1999 |
| JP | 2001-299772 | 10/2001 |
| JP | 2002-136520 | 5/2002 |

(Continued)

OTHER PUBLICATIONS

International Search Report dated Mar. 4, 2008 for corresponding PCT Application No. PCT/JP2008/000105.

(Continued)

*Primary Examiner* — Tse Chen
*Assistant Examiner* — Jason Ip
(74) *Attorney, Agent, or Firm* — Flynn, Thiel, Boutell & Tanis, P.C.

(57) ABSTRACT

An ultrasonograph contains a probe provided with a transmitting/receiving ultrasonic transducer at the center thereof, and the probe has a transmitting ultrasonic transducer and a receiving ultrasonic transducer which are symmetrically movable with respect to the transmitting/receiving ultrasonic transducer. Contacting the probe with the skin of a diagnosis area, a direction of the probe is adjusted to be perpendicular to the diagnosis object using echo signals of the transducer. Then the echo signals of the transmitting ultrasonic transducer and the transmitting/receiving ultrasonic transducer, and a distance between the ultrasonic transducers are processed to obtain a signal intensity. Results are displayed on a display to indicate the thickness, hardness of an articular cartilage, and a surface condition thereof visually so that it is possible to diagnose the articular cartilage without inserting a probe into the cavitas articulare.

6 Claims, 14 Drawing Sheets

FOREIGN PATENT DOCUMENTS

| | | |
|---|---|---|
| JP | 2002-345821 | 12/2002 |
| JP | 2005-253751 | 9/2005 |
| JP | 2005-526539 | 9/2005 |
| WO | WO 03/057000 A2 | 7/2003 |

OTHER PUBLICATIONS

"Review on Ultrasonic Evaluation by the Double Probe Technique (Ultrasonic Evaluation from Outside the Body)", Okamoto et al., Japan Machinery Society, Proceedings, 2006 Annual General Meeting, vol. 15, pp. 153-154 (2006).

"Measurement on Mechanical Characteristics of Articular Cartilage by Utilizing Ultrasonic Waves", Mori et al., Japan Clinical Biomechanics Society, 23, pp. 97-106, (2002).

"Seismic Ray Tracing Using Linear Traveltime Interpolation", Aikawa et al., Geophysical Prospecting, 41, pp. 99-111 (1993).

"Refraction Process Seismic Exploration Analysis Method Using Tomographical Techniques", Odahara et al., Koei Forum, 9, pp. 7-14, (2001).

"Ultrasonic Attenuation in Articular Cartilage", Senzid et al., Acoust. Soc. Am., 92 (2), pp. 676-681, (1992).

Yasunori Okamoto, et al., "Examination of ultrasonic measurement using two transducers (Evaluation for articular cartilage through the skin)", The Japan Society of Mechanical Engineers, Sep. 15, 2006; vol. 5; p. 153-154.

Koji Mori, et al., "Non-contact Evaluation for Articular Cartilage Using Ultrasound", Transactions of the Japan Society of Mechanical Engineers, Dec. 25, 2004, Series A, vol. 70, No. 700, pp. 1764-1771.

International Search Report dated Mar. 4, 2008 (2 pages).

* cited by examiner

ULTRASONOGRAPH

FIELD OF THE INVENTION

The invention relates to an ultrasonograph for diagnosing a condition of soft tissues such as an articular cartilage and a blood vessel in the vicinity of the skin of a body, by utilizing ultrasonic waves.

BACKGROUND OF THE INVENTION

It is well known that a method for directly observing the surface of a joint by inserting an arthroscope into the cavitas articulare, a method of intuitively diagnosing a degree of injury and hardness of the surface of a cartilage by contacting a probe with a damaged area of an articulara, a method for observing images picked up by the MRI, and so forth. With direct-vision observation by use of the arthroscope or the probe, however, none other than a surface state can be discriminated and it has been impossible to discriminate a crack present inside an articular cartilage. Similarly, it has been impossible to quantitatively determine the mechanics•structural characteristics of a subchondral bone area. Meanwhile, with the MRI method, it is impossible to observe a slight changes occurring in the cartilage. Further, it is difficult to make a diagnosis at a spotted area.

It is difficult to evaluate numerically the mechanics•structural characteristics of an articular cartilage by the conventional diagnostic methods, because the diagnosis criteria are not clear and the results are different depending on the observer. Further, in the numerical evaluation, the results are expressed with numbers, however, the operator might misread the numbers on a display, since the operator is engaged with several tasks simultaneously during a surgery operation.

Bones and articular cartilages have important roles for motions of the body and for supporting a body weight, therefore it is preferable that the bones are hard (high Young's modulus) and, in case of the articular cartilages, it is preferable that the hardness falls within a certain range because the articular cartilages contributes not only to the support of the body weight, but also to absorbing shock.

Similarly, blood vessels should have adequate hardness in order to fulfill its function for flowing pulsating blood because the blood vessels are susceptible to damage if they are excessively hard and unable to withstand blood pressure if excessively soft.

Ultrasonic signals reflect at a boundary of tissues having different acoustic impedances and it is possible to display a respective image of internal organs and tissues by utilizing the echo signals from the boundary. An acoustic velocity correlates with Young's modulus, which is an index of hardness, and when in measuring a substantially constant density material, the echo signals contain mechanical characteristics of the materials (See Non-patent document 1, and Non-patent document 2).

As shown in FIG. 1, a load-bearing part of a knee joint cartilage, which is likely susceptible to articular diseases, is moved to an area in the vicinity of the body surface when the knee is bent. The tissues of this area constitute a substantial laminar structure consisting of skin 4, articular cartilage 30 (several mm in thickness) and subchondral bone 31.

The skin 4 and the articular cartilage 30, among these tissues, containing rather much water, and have almost the same densities and relatively the same acoustic impedance although they have slightly different acoustic velocities. The subchondral bone 31 has larger values in both the acoustic velocity and density compared with those of the skin 4 and the articular cartilage 30, and has a significantly different acoustic impedance from both the skin 4 and the articular cartilage 30.

Patent document 1 JP 10-118062 A
Patent document 2 JP 2002-136520 A
Patent document 3 JP 11-316215 A
Patent document 4 JP S61 (1986)-290942 A
Patent document 5 JP 2002-345821A
Non-patent document 1 Ultrasonic Handbook by Ultrasonic Handbook Compilation Committee, published by Maruzen
Non-patent document 2 "Ultrasonic Waves and Material" by Japan Material Science Society, published by Shokabo
Non-patent document 3 "Review on Ultrasonic Evaluation by the Double Probe Technique (Ultrasonic Evaluation from Outside the body)" by Okamoto, Mori, et al., Japan Machinery Society, Proceedings, 2006 annual general meeting, Vol. 15, pp. 153-154, 2006

DISCLOSURE OF THE INVENTION

In Patent document 1, an objective of the invention is to obtain ultrasonic tomography images along with hardness. The hardness is determined on the basis of the variation in resonance frequency of a probe and the probe should be placed close to an object.

In Patent document 2, it is an object of the invention to evaluate the hardness of a living tissue. A bone is a measurement object and the hardness is estimated on the basis of the variation in resonance frequency of a probe and the probe must be in contact with the bone. In this method, it is difficult to make a probe contact with the bone and it is not clear to which extent the results are dependent.

Patent document 3 discloses an ultrasonic reflectscope for acquiring information on the position of defects such as a crack of an object by use of the TOFD (Time of Flight Diffraction) method. However, this method is based on an assumption that an acoustic velocity within the object is uniform. Therefore it is difficult to apply this method to living tissue comprising skin, an articular cartilage and a subchondral bone.

In Patent document 4, there is disclosed an apparatus displaying tomography images of living tissue and concurrently measuring an acoustic velocity and nonlinear acoustic parameters. However, since ultrasonic refraction is not taken into consideration for determining the acoustic velocity distribution, a positional accuracy in the acoustic velocity distribution is not accurate. Therefore, it is difficult to extract the surface roughness of the articular cartilage and minute cracks thereof.

In Patent document 5, there is disclosed a method for evaluating the hardness of an articular cartilage by utilizing the intensity of echo signals. With this method, the thickness of the articular cartilage can be concurrently evaluated. However, since the ultrasonic waves are directly emitted to the object, a probe must be inserted into the cavitas articulare. Consequently, it is impossible to observe the object through the skin.

Non-patent document 3 discloses the best location of a receiving ultrasonic transducer where the maximum echo signal from the evaluation target of the articular cartilage is received, while a transmitting ultrasonic transducer remains at a fixed position. However, no solution is disclosed as to how the apparatus is placed in relation to the area for the evaluation to obtain the maximum echo signal. Furthermore, characteristics of the articular cartilage correlated to the maximum echo signal and data necessary for evaluation of a degree of degeneration of the articular cartilage remain unclear.

The thickness and the hardness are considered to be important indices for evaluation of the articular cartilage. Further, as the smoothness of the surface of the articular cartilage decreases (formation of swells, from several tens to several hundreds of micrometers in length) due to the deterioration in articular disorder, small cracks occur to the surface of the articular cartilage. Therefore, the detection of such features is also useful for early diagnosis. Accordingly, it is important to acquire information on a shape such as the thickness, the surface roughness, along with the hardness.

It is therefore an object of the present invention to evaluate the thickness as well as the hardness of articular cartilage, nonuniformity of a surface of the articular cartilage, to detect cracks on the surface by emitting ultrasonic waves into a soft tissue inside the body from the surface of the body, and to display a state thereof so that one can recognize the state by intuition.

SUMMARY OF THE INVENTION

An ultrasonograph of this invention comprises a probe having a transmitting/receiving ultrasonic transducer provided at the center thereof, a pair of a transmitting ultrasonic transducer and a receiving ultrasonic transducer, one of which is disposed at the left side of the transmitting/receiving ultrasonic transducer and the other at the right side, or vice versa, the pair of transducers moving symmetrically with respect to the transmitting/receiving ultrasonic transducer in a lateral direction, a processor for calculating the signal intensity using echo signals of the receiving ultrasonic transducer at certain spaces of the transmitting ultrasonic transducer and the receiving ultrasonic transducer, and the echo signals of the transmitting/receiving ultrasonic transducer, and a display for displaying a relation between the calculated signal intensity and the distance between the transmitting ultrasonic transducer and receiving ultrasonic transducer, and echo signals of the transmitting/receiving ultrasonic transducer, thereby the ultrasonograph displays the thickness and hardness of an articular cartilage, and the surface condition thereof.

Further, an ultrasonograph of this invention, comprising a probe comprised of a transmitting/receiving ultrasonic transducer provided at the center thereof, a transmitting ultrasonic transducer provided at one side of the transmitting/receiving ultrasonic transducer and a receiving ultrasonic transducer on the other side thereof, the transmitting ultrasonic transducer and the receiving ultrasonic transducer moving independently in a lateral direction, a processor for calculating the acoustic velocity distribution across the cross-section of a diagnosis target using reflected signals of the receiving ultrasonic transducer, reflected signals of the transmitting/receiving ultrasonic transducer, and position data of the receiving ultrasonic transducer and the receiving ultrasonic transducer, and a display device for displaying the calculated acoustic velocity distribution, and a signal intensity from the transmitting/receiving ultrasonic transducer, thereby the ultrasonograph displays the thickness and hardness of an articular cartilage, and the surface condition thereof.

Figure 1:
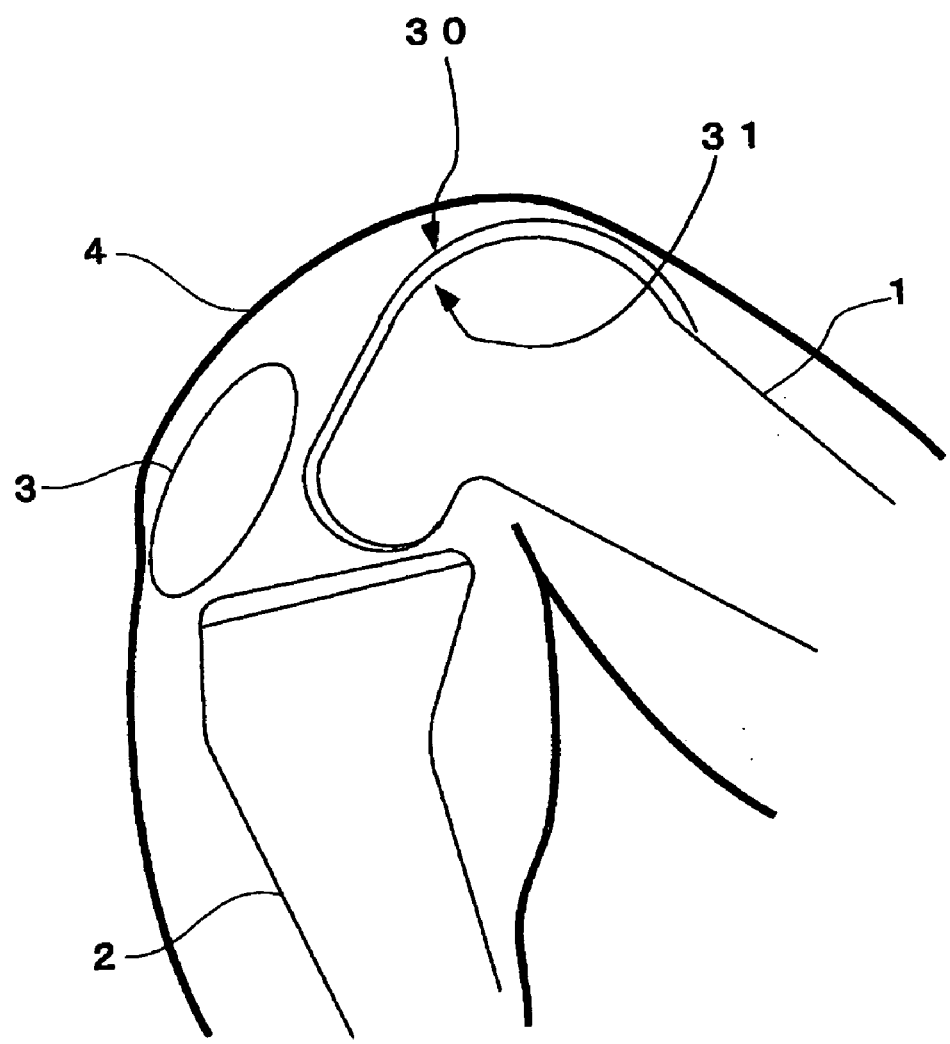
FIG. 1 is a schematic illustration showing relative positions of bones in the case of a bent knee joint.

1 a thighbone
2 a tibia
3 a kneecap
30 articular cartilage
31 subchondral bone
4 skin
5 probe
6 linear actuator
7 a transmitting and receiving transducer
8 a transmitting transducer
9 a receiving transducer
10 a linear slider
11 a link
12 reflecting wave from the articular cartilage
13 reflecting wave from the subchondral bone
14 display device
15 speed distribution display
16 processing unit
17 transducer distance measurement device
18 transducer distance controller

PREFERRED EMBODIMENT OF THE INVENTION

Embodiment 1

Embodiments of the ultrasonograph according to the invention are described hereinafter. Embodiment 1 is an ultrasonograph wherein an articular cartilage is a diagnosis object.

Figure 2:
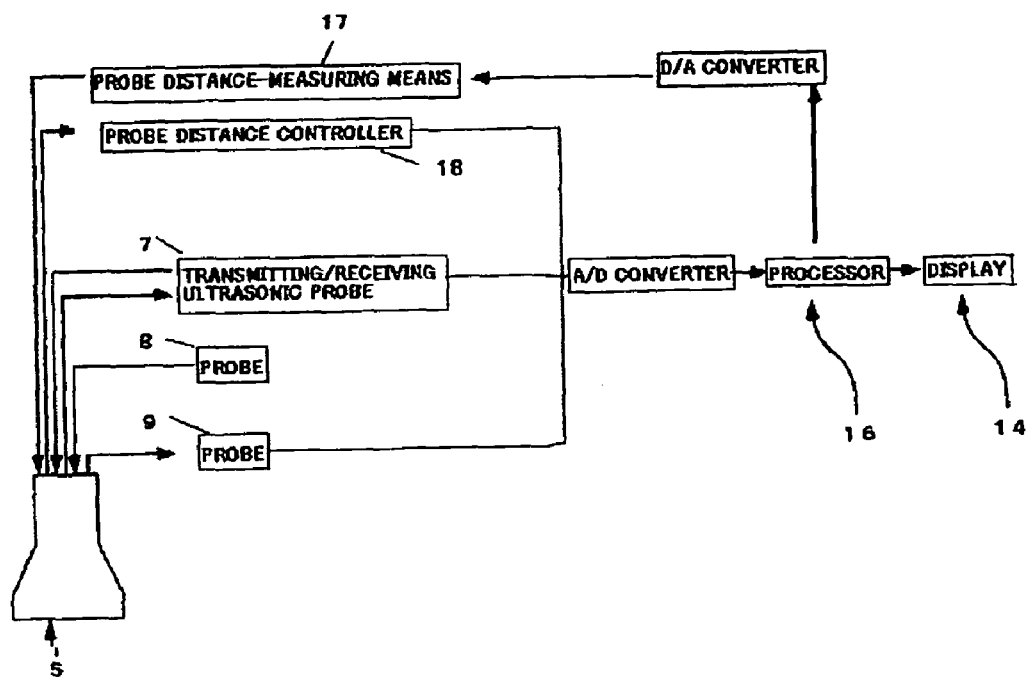
FIG. 2 is a block diagram of an embodiment of an ultrasonograph according to the invention.
Figure 3:
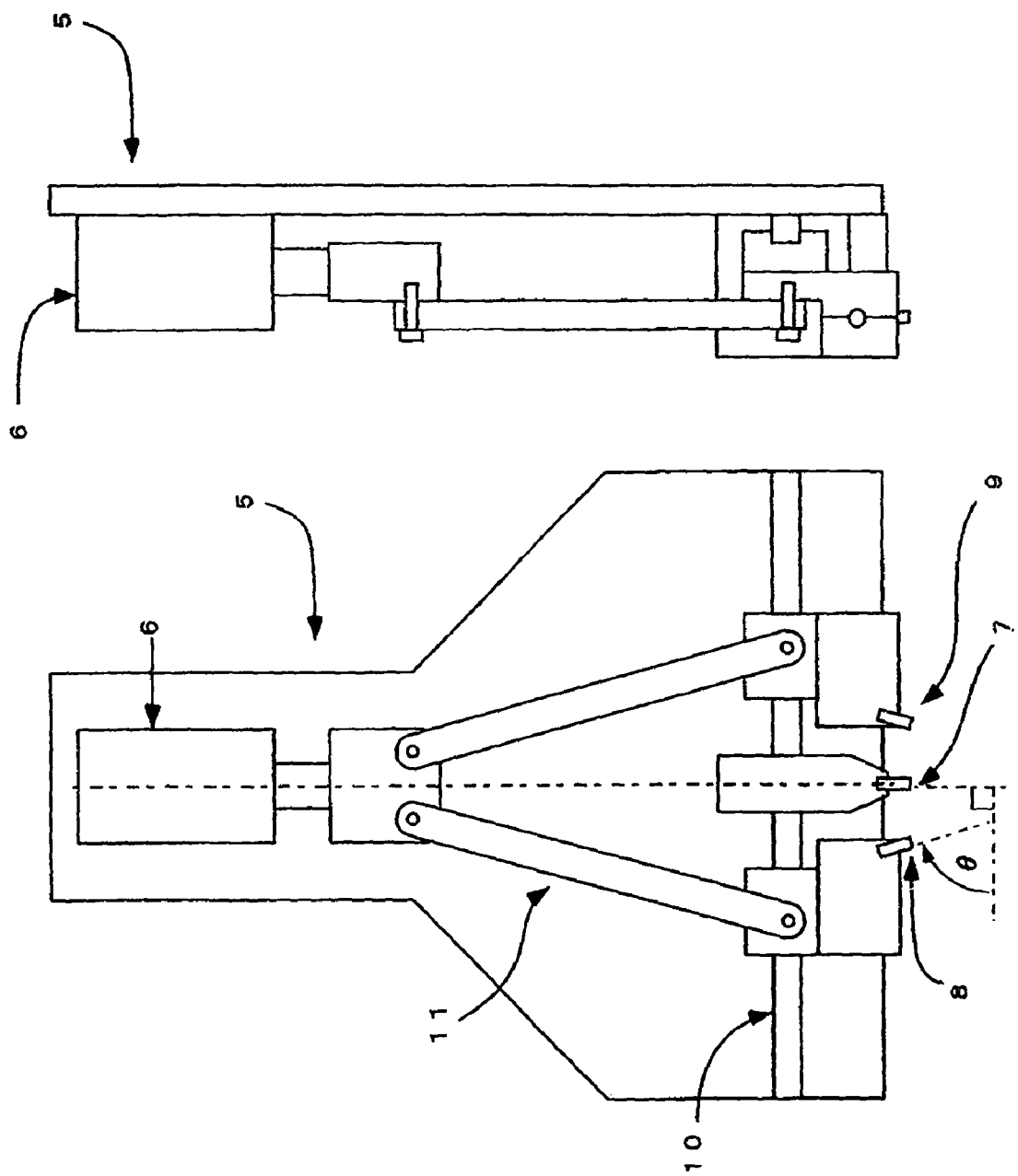
FIG. 3 is a front view of a probe of the ultrasonograph according to the invention.
Figure 4:
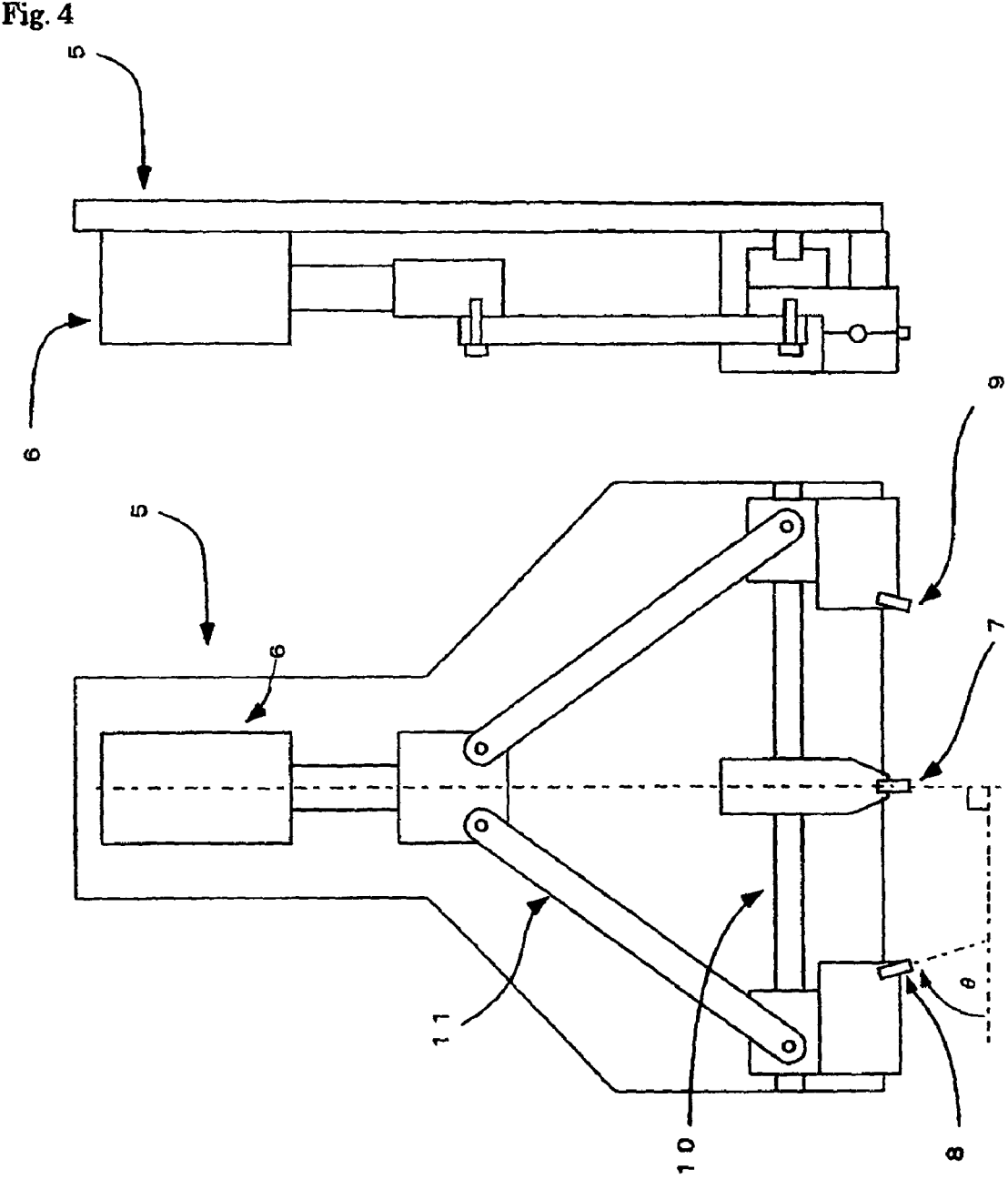
FIG. 4 is a front view of the probe of the ultrasonograph according to the invention when an interval between the ultrasonic transducers of the probe of the ultrasonograph is expanded.
Figure 14:
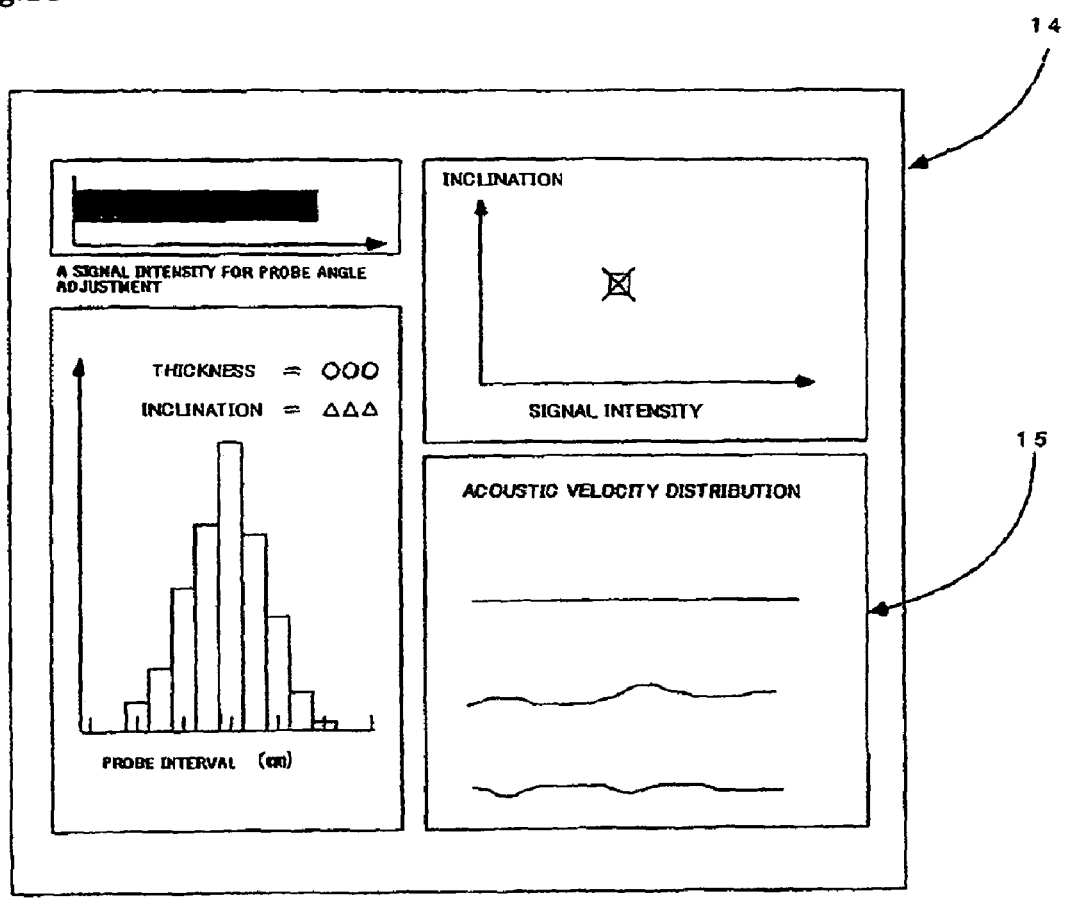
FIG. 14 is a schematic illustration showing an example of a display screen.

As shown in FIGS. 2 and 3, a probe 5 of the ultrasonograph is provided with a transmitting/receiving ultrasonic transducer 7 at the central part thereof and a pair of a transmitting ultrasonic transducer 8 and a receiving ultrasonic transducer 9 disposed symmetrically at both sides of the transmitting/receiving ultrasonic transducer 7 at an angle θ with respect to an object plane. The pair of the transducers 8, 9 moves symmetrically with respect to the transmitting ultrasonic transducer 8 in a lateral direction along a linear slider 10 actuated as shown in FIGS. 3 and 4 by one linear actuator 6 via a link 11 system. Further, a distance-measuring device 17 determines the distance between the ultrasonic transducers 8 and 9 (referred to as the transducer distance hereinafter) by detecting the location of the transducers 8 and 9. A distance controller 18 controls the transducer distance to a predetermined value. A processor 16 processes echo signals reflected from a diagnosis target and a display 14 displays processed results as shown in FIG. 14, such as an echo signal intensity received by the transmitting/receiving ultrasonic transducer 7, and so forth.

The transmitting/receiving ultrasonic transducer 7 and the transmitting ultrasonic transducer 8, assembled in the probe 5, are all of a cylindrical shape of 2 mm diameter and 2 mm height, and transmit a plane wave of 15 MHz as central frequency.

Figure 5:
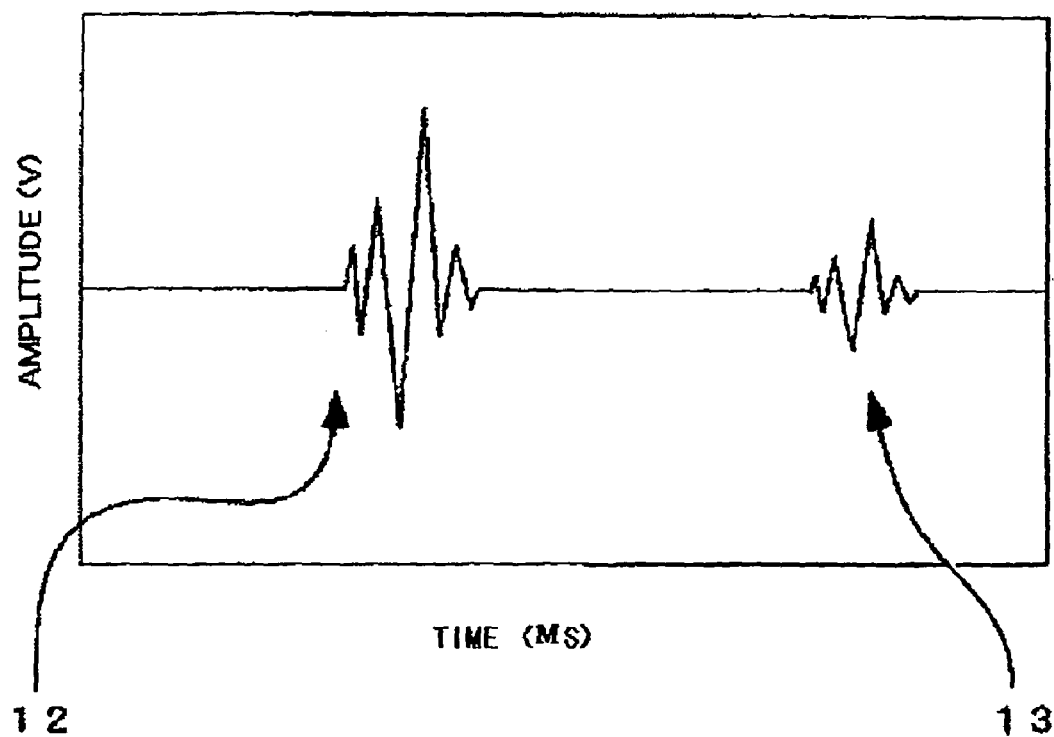
FIG. 5 a schematic illustration showing a echo signal from an articular cartilage.

When an ultrasonic wave is emitted to the articular cartilage 30, an echo signal 12 from the surface of the articular cartilage and an echo signal 13 from the subchondral bone are detected, as shown in FIG. 5. However, if respective angles of the transmitting/receiving ultrasonic transducer 7 and the transmitting ultrasonic transducer 8, against the surface of the articular cartilage 30 are not proper, echo signals from the surface of the articular cartilage 30 and the echo signals from the subchondral bone 31 cannot be separately detected and it is therefore important to adjust the angle of the probe 5 against the surface of the articular cartilage 30.

The proper angle of the probe 5 against the articular cartilage is determined by the following procedure.

First, the probe 5 is applied to the body surface and the angle of the probe 5 against the diagnosis object is varied while the ultrasonic waves are emitted from the transmitting/receiving ultrasonic transducer 7. When the maximum echo signal from the articular cartilage 30 is detected by the transmitting/receiving ultrasonic transducer 7, the probe 5 is fixed at this angle.

Then, a pair of the transducers 8 and 9 is moved symmetrically with respect to the transmitting/receiving ultrasonic transducer 7 in the lateral direction by the actuator 6, thereby changing the transducer distance, then an intensity of an echo signal received by the receiving ultrasonic 9 transducer varies. When the receiving ultrasonic transducer 9 detects a maximum echo signal at certain positions of the transducers 8 and 9, then the actuator 6 stops and the probe 5 is fixed at this position.

Figure 6:
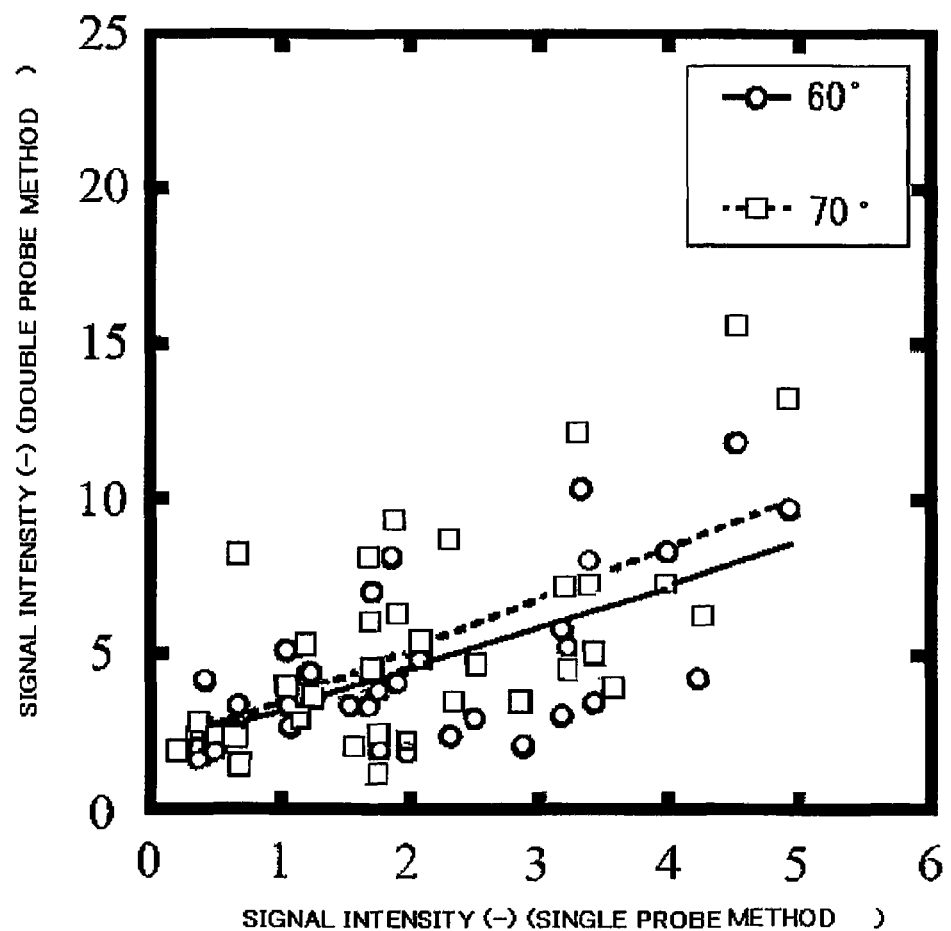
FIG. 6 is a graph showing a correlation between signal intensity for measurement by transmitting and receiving ultrasonic waves, and signal intensity of a echo signal from a transmitting ultrasonic transducer.

It is known that Aggregate modulus corresponds to Young's modulus of the articular cartilage, and that there is a correlation between the echo signal intensity emitted vertically to the articular cartilage (the single transducer method) and the Aggregate modulus. As shown in FIG. 6, it is known that a signal intensity obtained by the double transducer method using a pair of ultrasonic transducers, one for transmission and the other for receiving, has a correlation with an echo signal intensity obtained by the one transducer method. (See, for example, "Measurement on Mechanical Characteristics of Articular Cartilage by Utilizing Ultrasonic Waves" by Mori, et al., publication by Japan Clinical Biomechanics Society, 23, pp. 97-106, 2002).

Further, the data shown in FIG. 6 was obtained when the pair of ultrasonic transducers 8 and 9 were at angles of 60°, and 70°, respectively.

Therefore, an echo signal intensity received by the receiving ultrasonic transducer 9 correlates to Aggregate modulus corresponding to Young's modulus of the articular cartilage. The signal intensity can be obtained by square value of the echo signal, and on the basis of the maximum value of the square of the echo signal, but if the echo signal is subjected to wavelet transformation, noises are easily separated, and the echo signals become clear. Therefore, it is preferable to apply the echo signals to the wavelet transformation, so that the processor 16 is installed with a wavelet transformation program.

The waveform of an ultrasonic wave generally consists of at least two sine waves, if a chirp wave is used as a transmitting wave and upon signal reception, noises are greatly reduced by determining a self-correlation function between the received echo signal wave and the chirp wave. Therefore it is preferable to use the chirp wave as the transmitting wave.

For simulating a diagnosis of a state of an articular cartilage through a skin, a specimen of an articular cartilage covered with a skin was placed at the bottom of a water tank and the specimen of the articular cartilage was immersed in a physiological salt solution and being subjected to a test.

Further, in order to artificially simulate the damages inflicted on the articular cartilage, the articular cartilage was treated by a collagenase enzyme solution and the damaged surface was artificially generated. The damages became greater as the collagenase treatment time became longer.

Figure 7:
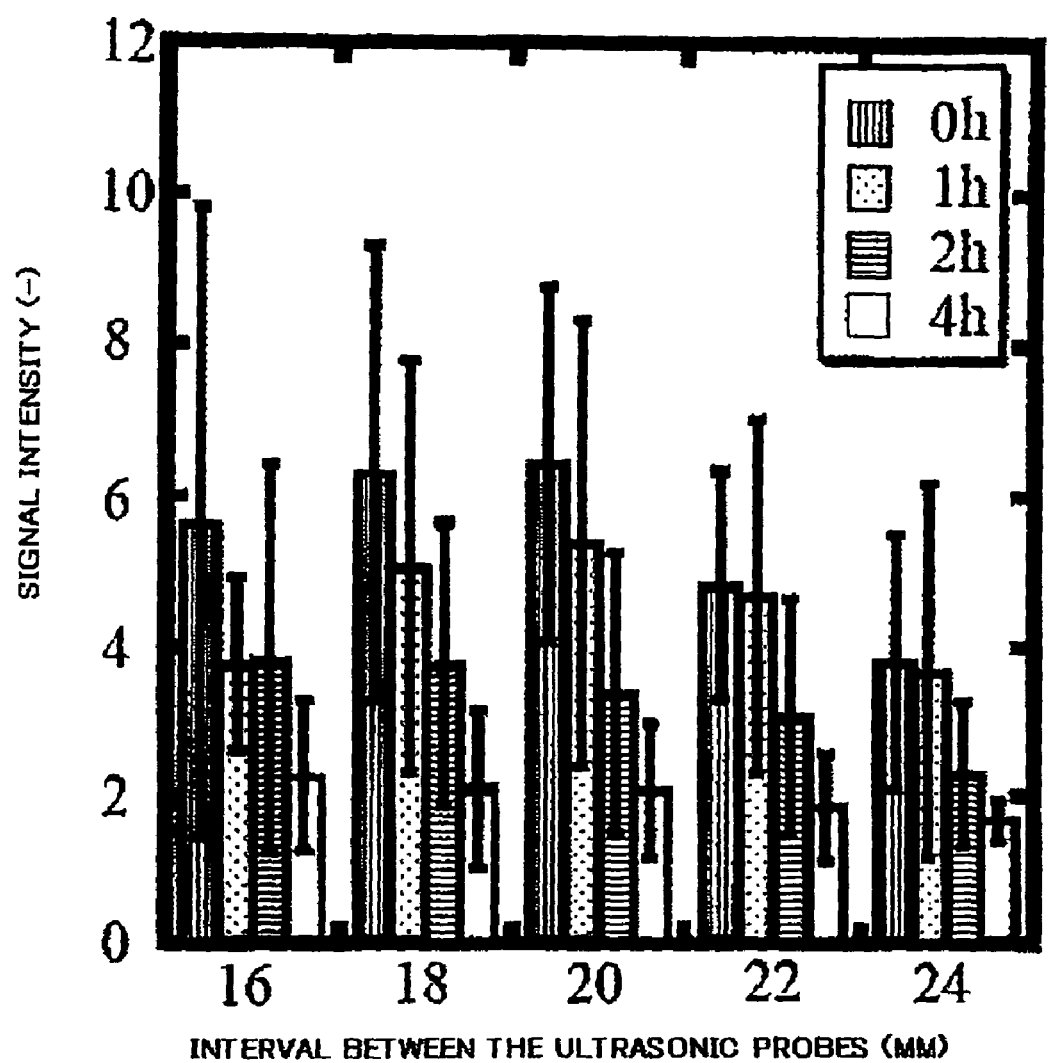
FIG. 7 is a graph showing a relation between the interval between the ultrasonic transducers, and signal intensity variation by the collagenase treatment time length.

FIG. 7 is a graph showing the signal intensity versus the transducer distance at each collagenase treatment time (the degree of damage of the cartilage) with an installation angle (an emitting angle of the ultrasonic wave) of the ultrasonic transducer 8 at 60 degrees with respect to the diagnosis target plane of the articular cartilage.

The graph shows a tendency that as the collagenase treatment time increases, the maximum signal intensity decreases at any of the transducer distances, a maximum signal intensity of the echo signal is observed at the transducer distance of 20 mm. Further, as the transducer distance deviates from the central value of 20 mm, the signal intensity decreases. Other than the transducer distance of the maximum signal intensity, the signal intensity changes depending on the transducer distance. The degree of change becomes small as the transducer distance is away from 20 mm.

Figure 8:
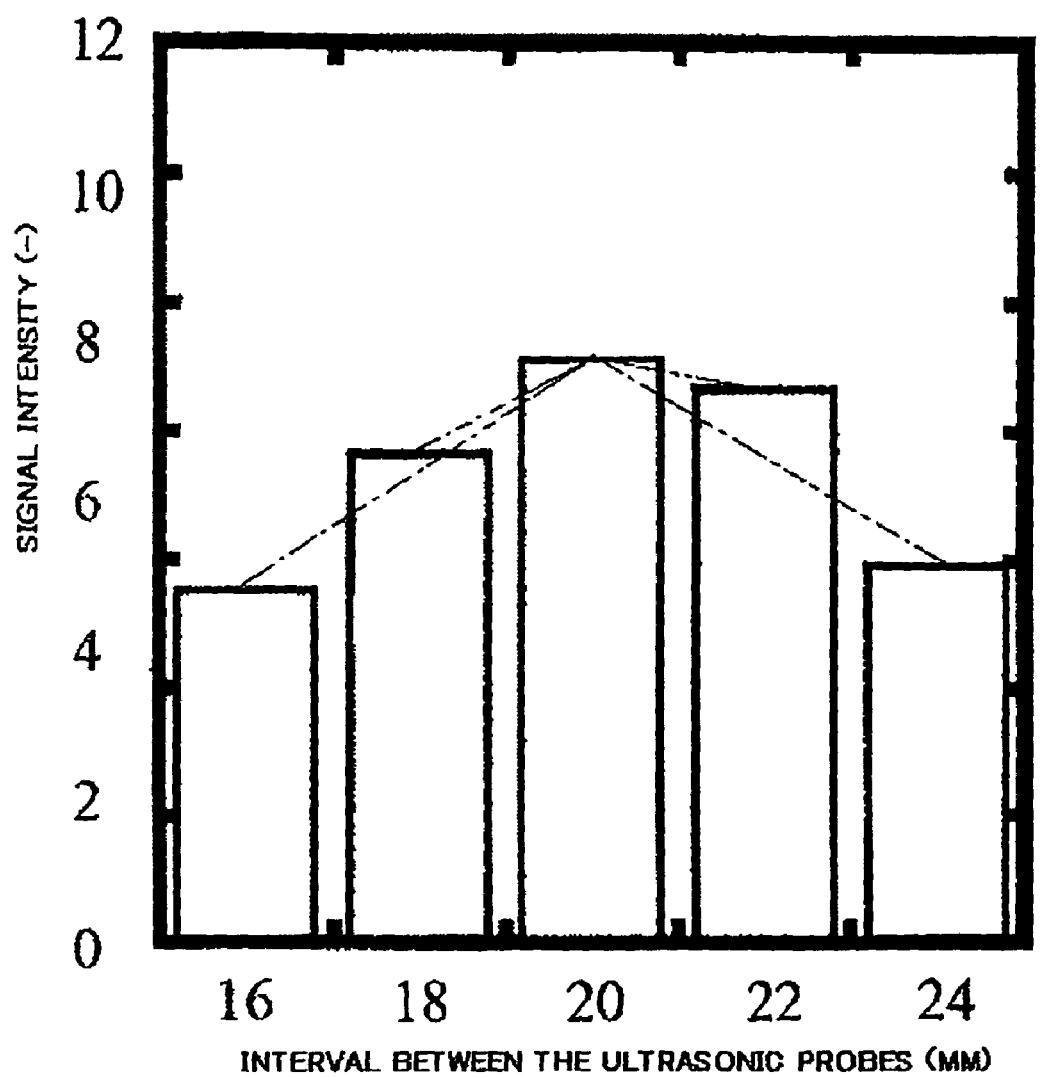
FIG. 8 is a graph showing a relation between the interval between the ultrasonic transducers, and signal intensity, for every collagenase treatment time length.

The transducer distance, where the maximum echo signal intensity of each damage degree of an articular cartilage, is adopted as a reference distance. A ratio of the echo signal intensity deviation from the maximum value and the transducer distance deviation from the reference distance, that is expressed as (signal intensity deviation)/(transducer distance deviation) is shown as an inclined dotted line from the maximum echo signal value to each echo signal intensity at certain transducer distances in FIG. 8.

Figure 9:
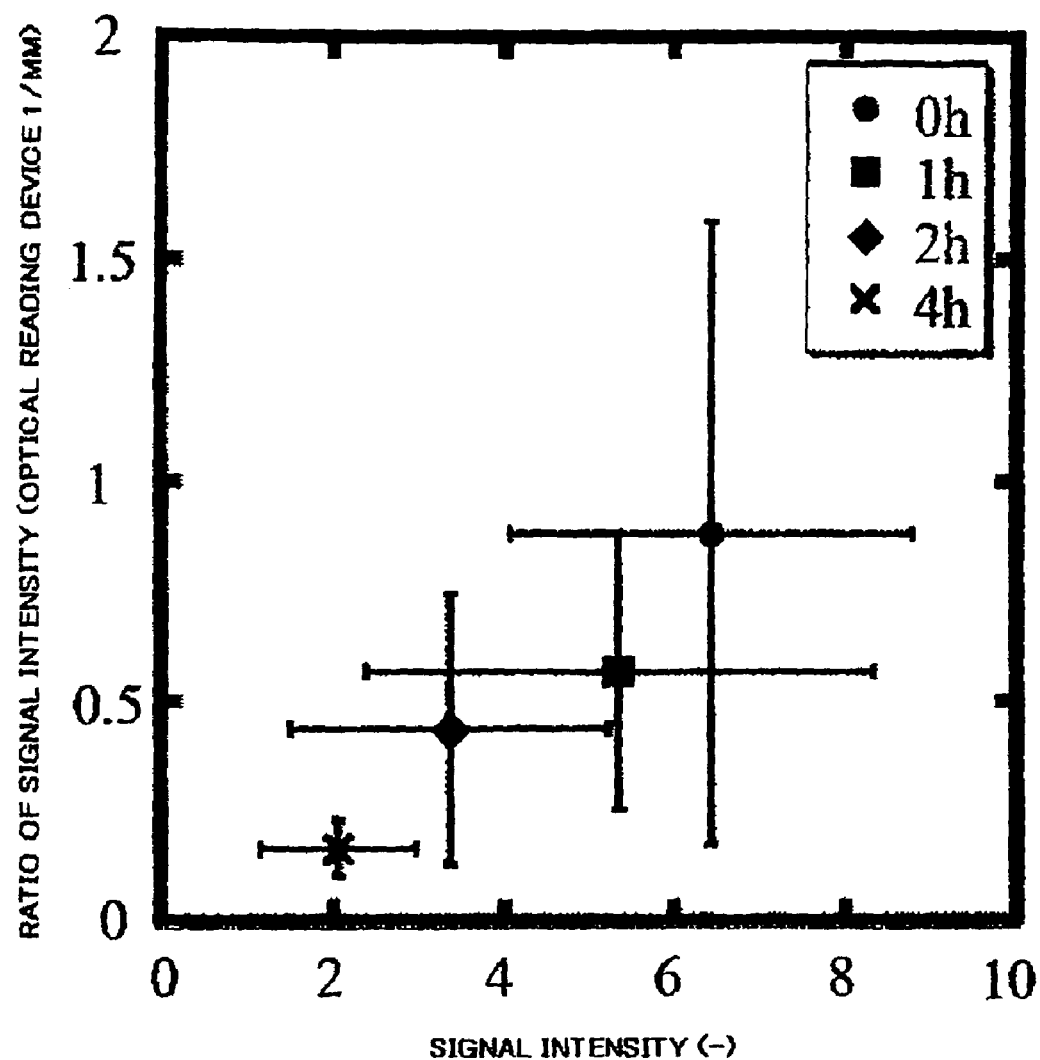
FIG. 9 is a graph showing a relation between signal intensity, and (signal intensity variation)/(interval variation)

As shown in FIG. 9, plotting the values of the ratio on a graph expressing the ratio of signal intensity difference along the vertical axis and the echo signal intensity along the horizontal axis, the respective values are almost on a straight line according to the collagenase treatment time, that is, the degree of damage of the articular cartilage. Accordingly, it is possible to evaluate the degree of damage quantitatively and visually by the location of the plots. More specifically, when the plots are in the upper right area of the graph, the specimen is considered to be normal and, on the other hand, the plots are in the lower left area, the specimen is considered to be damaged.

Figure 10:
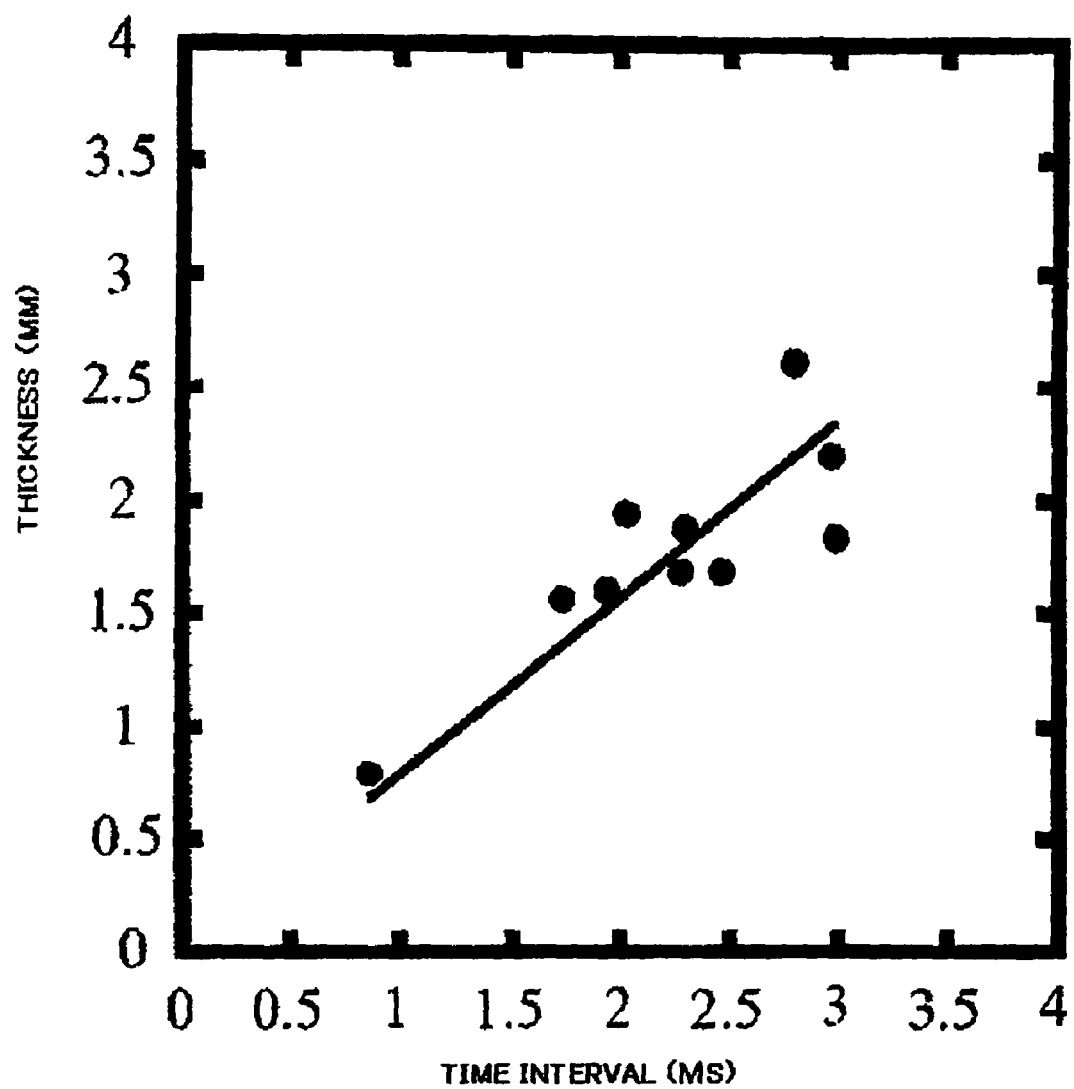
FIG. 10 is a graph showing a relation between a time interval between a echo signal from the surface of the articular cartilage, and a echo signal from the subchondral bone, and thickness of the articular cartilage.

In FIG. 10, a correlation between the thickness of the articular cartilage 30 and time difference between the echo signal from the surface of the articular cartilage 30 and from the subchondral bone 31 at the transducer distance where the echo signal intensity is maximum.

The thickness of the articular cartilage 30 is obtained from the time difference of the echo signals since the thickness of the articular cartilage 30 is proportional to the time difference between the two peaks of echo signals received by the receiving ultrasonic transducer 9 at the transducer distance of the maximum signal intensity.

Thus, the probe 5 is secured at the angle where the echo signal from the articular cartilage 30 received by the transmitting/receiving ultrasonic transducer 7 is at a maximum value. The Aggregate modulus corresponding to Young's modulus of the articular cartilage 30 is obtained, thereby evaluating the hardness of the articular cartilage 30.

The preferable angle θ of the ultrasonic transducer 8, 9 with respect to the diagnosis target plane is between 45 to 85 degrees. If the angle θ is smaller than 45 degrees, the echo signals can not be received under the influence of a curvature of the surface of the articular cartilage, or refraction while passing through the skin, a rather greater angle is preferable. On the other hand, if the angle θ is too large, the echo signals will be influenced by the slope of the articular cartilage, therefore, a more preferable angle θ ranges from 60 to 75 degrees.

To determine the transducer distance for obtaining a maximum echo signal, the transducer distance is varied with certain intervals. It is preferable with a small distance interval for obtaining an accurate transducer distance. It takes a longer time to find an appropriate transducer distance, it is preferable to vary the transducer distance at an interval of 0.10 mm to 0.50 mm.

The central frequency of the ultrasonic waves is preferably in a range of 1 to 20 MHz and if the high frequency is used, the space resolution becomes higher, however, the ultrasonic waves are influenced by small property changes of tissues when passing through living tissues. Further, the higher the ultrasonic frequency, the greater the attenuation of the ultrasonic waves, the echo signal will have much noises and the intensity of the echo signal decreases. Accordingly, considering the trade off between the spatial resolution and the echo signal intensity, the preferable center frequency of the ultrasonic waves is in a range of 3 to 10 MHz.

The transducer distance-echo signal intensity correlation may be obtained by moving either of the transmitting ultrasonic transducer 8 or the receiving ultrasonic transducer 9 independently, but an actual ultrasonic wave reflecting point is not identical to a point where the maximum echo signal is obtained by the transmitting/receiving ultrasonic transducer 7, therefore, it is not certain that the probe 5 is correctly placed perpendicular to the diagnosis area. For this reason, a pair of the transmitting and the receiving ultrasonic transducers 8 and 9 should be moved symmetrically with respect to the transmitting/receiving ultrasonic transducer 7.

Detection of the locations of the transmitting ultrasonic transducers 8 and the receiving ultrasonic transducer 9 is executed by an appropriate location-detecting means, for example, by a laser displacement gauge, and calculating means for obtaining a distance between them. If a stepping motor is used to drive the linear actuator 6, the distance is calculated using a rotation angle of the stepping motor.

A transducer array comprising a plurality of transmitting ultrasonic transducers 8 and a plurality of receiving ultrasonic transducers 9 are symmetrically arranged with respect to the transmitting/receiving ultrasonic transducer 7 located at the center of the device and a switching transmission and reception sequentially for scanning the articular cartilage electronically. Therefore, the mechanical scanning system is not necessary, the device rarely becomes out of order, and it is possible to change the transmission and reception position of the transducers rapidly (more than 10 to 30 times per second) compared with the mechanical scanning. However, electronic scanning requires a plurality of ultrasonic transducers, which brings a cost increasing problem.

In this invention, the transducer distance should be changed with the precision of from 0.10 mm to 0.50 mm, but the scanning speed is not necessarily high, either the mechanical scanning or the electronic scanning should be selected considering the cost of the device.

Embodiment 2

Figure 11:
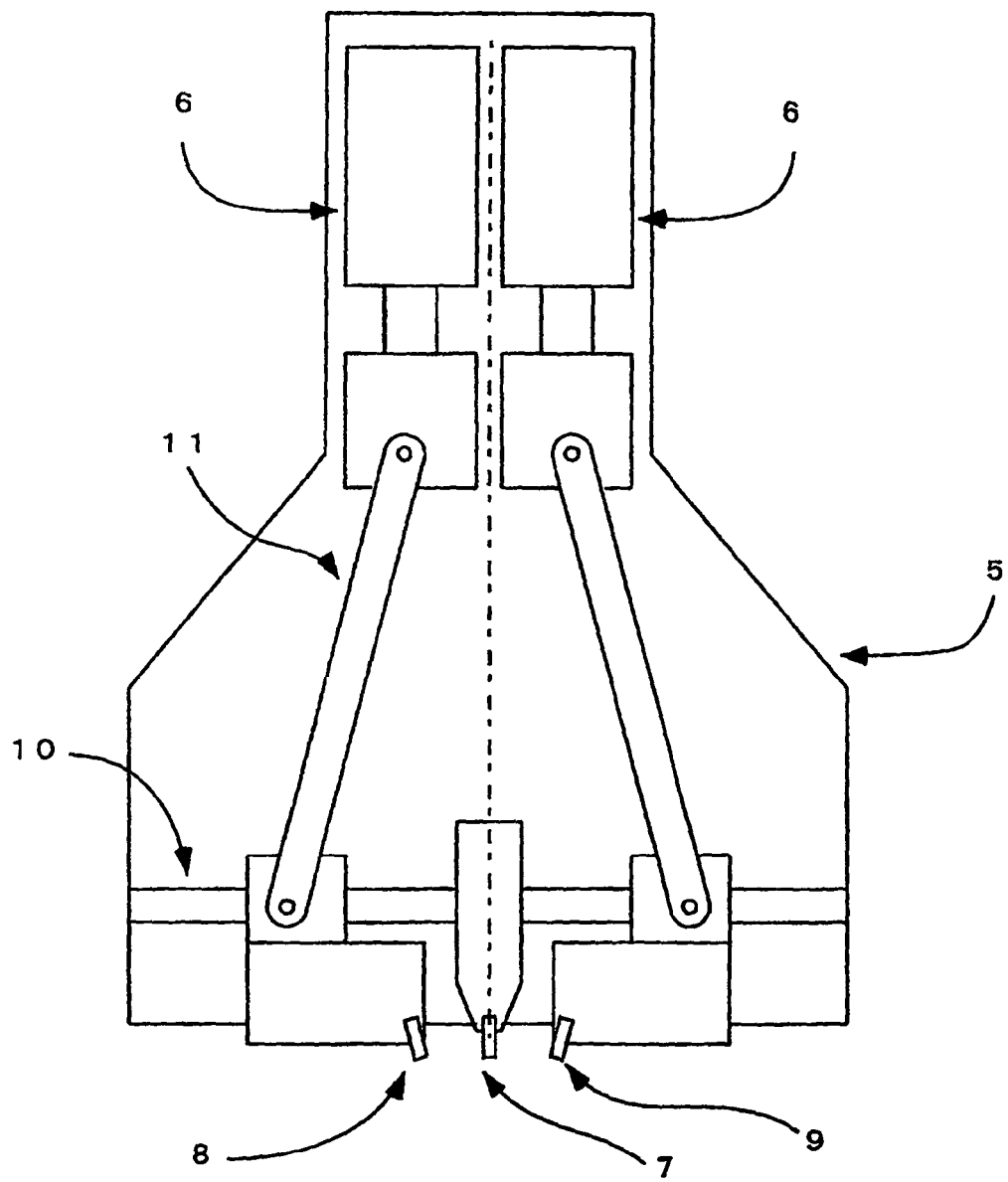
FIG. 11 is a front view of a probe of an ultrasonograph according to Embodiment 2 of the invention, capable of independently moving a transmitting ultrasonic transducer, and a receiving ultrasonic transducer.

As shown in FIG. 11, an ultrasonograph of Embodiment 2, essentially identical to Embodiment 1, comprises a transmitting/receiving ultrasonic transducer 7 located at the center of the device, for checking whether a probe 5 is perpendicular to an articular cartilage which is a diagnosis object, a transmitting ultrasonic transducer 8 and a receiving ultrasonic transducer 9 disposed symmetrically with respect to the transmitting/receiving ultrasonic transducer 7 and linear actuators 6 driving the transducers 8, 9 symmetrically and laterally for scanning. Each transducer 8, 9 has its own linear actuator 6 for independent driving along a linear slider 10.

Figure 12:
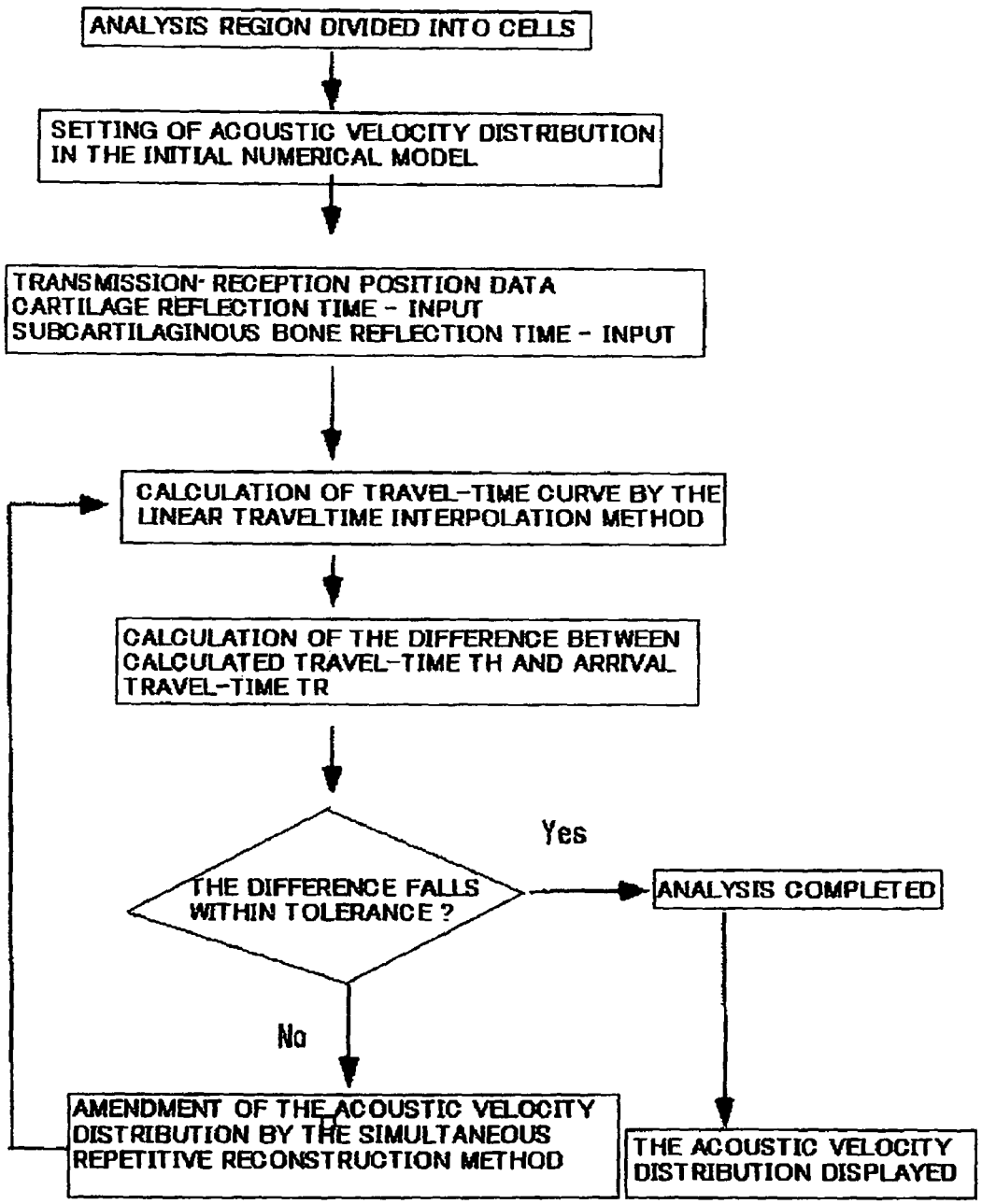
FIG. 12 is a flow chart showing an analysis procedure for acquiring acoustic velocity distribution.

FIG. 12 indicates a process for determining an acoustic velocity distribution in a diagnosis target.

Figure 13:
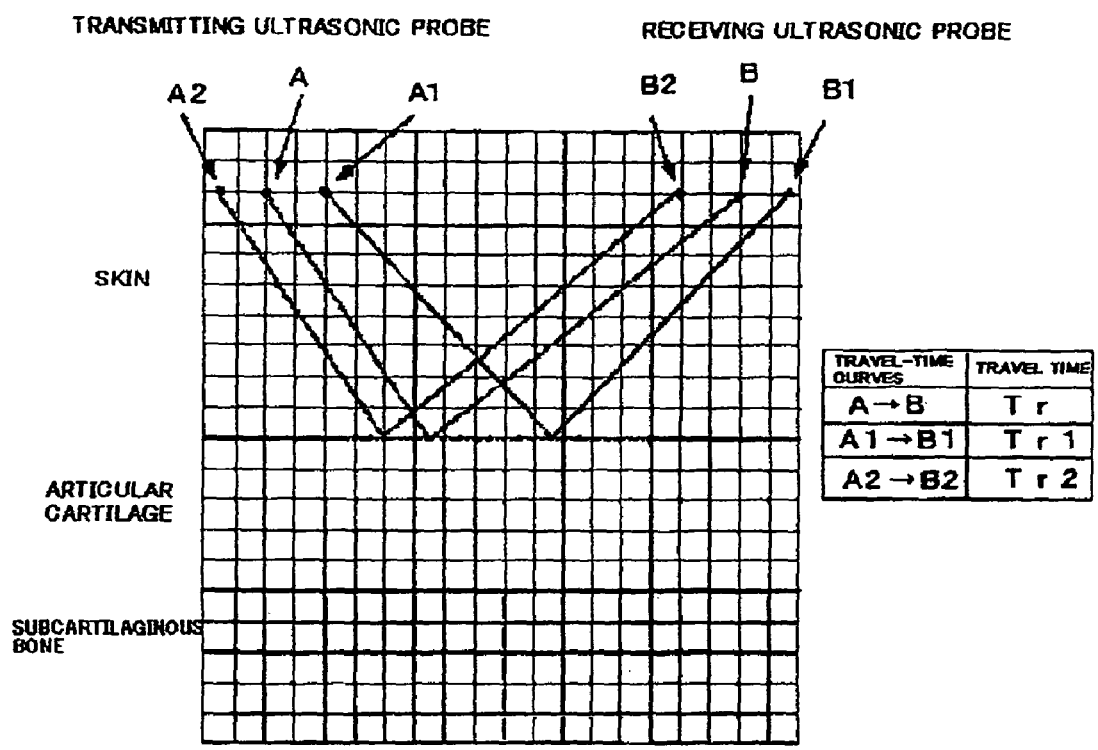
FIG. 13 is a conceptual view showing travel-time curves in a numerical model of cells.

As shown in a schematic diagram of FIG. 13, in which the transmitting ultrasonic transducer 8 is fixed at a certain position A, then the linear actuator 6 drives the receiving ultrasonic transducer 9 along the linear slider 10 in lateral direction for scanning the surface of the articular cartilage 30, a position of the receiving ultrasonic transducer 9 is determined using an ultrasonic transducer distance detecting means 17 and echo signals received by the transducer 9 at each position are stored.

Subsequently, the fixed position of the transmitting ultrasonic transducer 8 is changed to a position Al, and the receiving transducer 9 is also moved along the linear slider and the echo signals at each position are stored. The scanning process is executed repeatedly, and a set of the positions of transmitting transducer 8, positions of the receiving transducer 9 and echo signals at each positions are stored in a memory of a processor 16.

An area of diagnosis is divided into cells as appropriate to construct a numerical model, thereby calculating the time (hereinafter referred to as cartilage reflection time) between the signal stored and an echo signal from the surface of the articular cartilage 30, and time (hereinafter referred to as subchondral bone reflection time) between the signal stored and an echo signal from the subchondral bone 31. Travel-time curves are determined on the basis of the plurality of positions of the transmitting transducer 8 and the positions of the receiving transducer 9, together with the cartilage reflection time and the subchondral bone reflection time.

Assuming the velocity of the ultrasonic waves in each cell is constant and the ultrasonic waves propagate straight without refraction through the cell. Refraction takes place when the ultrasonic waves passing through the cell have different velocities in adjacent cells. Thus, a travel-time curve is expressed as a polygon made up of a multitude of straight lines. Further, the elapsed time Tr (travel-time) is also determined.

The travel-time is determined using, for example, the linear travel-time interpolation method by Aikawa, et al. (reference:

"Seismic Ray Tracing using linear traveltime interpolation", by Aikawa and Kawada, Geophysical Prospecting, 41, pp. 99-111, 1993).

Since the mean acoustic velocities of skin, fat, articular liquid, an articular cartilage, and a subchondral bone are known (see Non-patent document 1), an initial velocity structure (acoustic velocity distribution) of the numerical model is determined using the above-mentioned mean velocities.

The time difference between the predicted travel-time Th and the detected travel-time Tr is calculated for every travel-time curve, and the acoustic velocities in the respective cells are corrected such that the time differences will become minimum. For correcting the velocities, the simultaneous repetitive reconstruction method (see "geophysical prospecting for construction-disaster-prevention engineers", by Sasa Kohichi, et al., published by Morikita Publishing Co., Ltd.) is used.

Unless the time difference falls within an allowable value, the travel-time curve is repeatedly corrected following the above-mentioned correction process, (see "Refraction Process Seismic Exploration Analysis Method using tomographical techniques" by Odahara, et al., Koei Forum, 9, pp. 7-14, 2001).

A converged velocity distribution is considered to be the velocity distribution of the area through which the ultrasonic wave has passed. An acoustic velocity has a correlation with the Young's modulus, and a live body contains a lot of water. Except for hard tissues, such as bones, tissues other than bones have almost the same density deviating within 10%, therefore it is possible to determine the hardness (Young's modulus) of articular cartilage utilizing the acoustic velocity distribution.

As the acoustic velocity in the articular cartilage is about 1600 m/s while the acoustic velocity in the skin is about 1200 m/s, an acoustic velocity in the fat is about 1400 m/s, and an acoustic velocity in the subchondral bone is about 3500 m/s, it is easy to distinguish the articular cartilage from other tissues by evaluating the acoustic velocity distribution of the area and one can estimate the thickness and surface roughness of the cartilage.

Further, the smaller cells will provide a more accurate prediction of minute swells and minute cracks on the surface of the articular cartilage.

For obtaining more accurate acoustic velocity distribution, it is necessary to use travel-time curves, a number of the travel-time curves being caused to pass through the area of the measurement target by independently moving the respective positions of the bilaterally disposed ultrasonic transducers. Furthermore, the bilaterally disposed ultrasonic transducers are moved along an arc-like manner with the use of a linear slider 10 formed in the shape of an arc, instead of linear movement of the bilaterally disposed ultrasonic transducers.

Since not only ultrasonic velocity but also an attenuation of the signal (attenuation coefficient) during the propagation differs from one living tissue (an organ) to another and the attenuation coefficient varies depending on the degree of damage of the organ, it is possible to identify an organ and to evaluate the damage with the attenuation coefficient. It has been reported that an attenuation coefficient of the cartilage changes when heavily loaded, which suggests that a damaged cartilage with a heavy load can be identified by determining the attenuation coefficient (see "Ultrasonic attenuation in articular cartilage" by Senzig, A. D., Forster, K. F, and Olerud, J. E., J. Acoust. Soc. Am., et al., 92 (2), (1992), pp. 676-681).

A distribution of the attenuation coefficient can be obtained by the same procedure as shown in FIG. 12, however, an amplitudes of the echo signals is required, it is difficult to obtain a true attenuation coefficient distribution because the amplitudes are disturbed by noises. On the other hand, in case of the acoustic velocity distribution, the amplitude of the echo signals are not necessary, but only the reflection time from the cartilage and the subchondral bone are required, therefore the acoustic velocity distribution is rarely disturbed by noises, and the method is practical.

In the ultrasonograph of Embodiment 2, the signal emitted from the transmitting transducer 8 is received by the receiving transducer 9, whereupon an acoustic velocity distribution is acquired according to the procedure shown in FIG. 12, so that the transmitting/receiving ultrasonic transducer 7 located at the center of the device is not an indispensable component. Since two reflection times from the cartilage and the subchondral bone are detected from one reception signal, it is possible to determine a detailed acoustic velocity distribution with fewer numbers of measuring points (fewer combinations of the transmitting ultrasonic transducer 8 and the receiving ultrasonic transducer 9).

However, if the position of the probe 5 is deviated from being perpendicular to the articular cartilage, the ultrasonic wave emitted from the transmitting ultrasonic transducer 8 is not reflected in the direction of the receiving ultrasonic transducer 9, so that the echo signals from either of the articular cartilage or the subchondral bone cannot be detected. Accordingly, when the probe 5 is disposed perpendicular to the articular cartilage, the echo signals from the respective surfaces of the articular cartilage and the subchondral bone are likely received by the receiving transducer, the transmitting/receiving transducer 7 is disposed at the center of the device for detecting the direction of the transducer.

An example of various types of information of the articular cartilage, detected by the ultrasonograph of the embodiment 1 or 2 displayed on the display 14 is shown in FIG. 14. The signal intensity of the transmitting/receiving ultrasonic transducer 7 for indicating whether the probe 5 is positioned at an adequate angle is displayed by a horizontal bar at the upper left corner of the display 14. An operator can visually recognize whether the angle of the probe 5 is adequate or not.

According to the relation between the ratio of signal intensity variation (the transducer distance)—the maximum signal intensity as shown in FIG. 9, the obtained result of the thickness and the inclination value (the signal intensity variation)/(the transducer interval variation) are displayed numerically at the upper right. Further, by displaying the signal intensity and the inclination, together with the acoustic velocity distribution, one can understand the state of the damage of the articular cartilage, minute swells, and minute cracks visually.

The surface of a normal articular cartilage is smooth, but once the surface is damaged with cracks and defects, the surface becomes uneven and is no longer smooth. By visualizing the velocity distribution inside the articular cartilage, one can tell the state thereof by analyzing the velocity distribution. In the visualized velocity distribution, if a boundary between the articular cartilage and the skin area is indicated as a straight line, the surface is considered to be smooth and in the normal state. If the boundary is indicated as a curved line having a small unevenness, one can tell that there might exist small bumps and pits on the surface of the articular cartilage.

INDUSTRIAL APPLICABILITY

According to the present invention, it is possible to obtain the thickness as well as hardness of an articular cartilage, minute swells, minute cracks of the articular cartilage without inserting a probe into a cavitas articulare. Further, it is possible to obtain the thickness as well as hardness of a blood vessel in the vicinity of the skin, minute swells, minute cracks of the blood vessel through the skin and it is possible to diagnose a progress state of a disorder of the articular cartilage through the skin. It is also possible to determine the thickness as well as hardness of a bone in the vicinity of the skin, minute swells and minute cracks through the skin.

The invention claimed is:

1. A diagnostic ultrasonograph comprising:
a probe housing a transmitting and receiving ultrasonic transducer provided at a central location thereof configured to determine a proper orientation angle of the probe, a transmitting ultrasonic transducer provided at a first side of the transmitting and receiving ultrasonic transducer and a receiving ultrasonic transducer provided at a side of the transmitting and receiving ultrasonic transducer opposite to the first side, the transmitting ultrasonic transducer and the receiving ultrasonic transducer being configured to move symmetrically in a lateral direction with respect to the transmitting and receiving ultrasonic transducer;
means for obtaining positioning data for the transmitting ultrasonic transducer and receiving ultrasonic transducer;
a processor configured to calculate the distance between the transmitting ultrasonic transducer and the receiving ultrasonic transducer based on the positioning data, signal intensities at each distance based on received echo signals from a diagnosis target based on echo signals received by the transmitting and receiving ultrasonic transducer; and
a display configured to display graphically a relation of the signal intensity and the distances and the intensity of the echo signal received by the transmitting and receiving ultrasonic transducer.

2. The ultrasonograph according to claim 1, wherein the distance between the transmitting ultrasonic transducer and receiving ultrasonic transducer determines a maximum signal intensity as a central value and a (signal intensity deviation)/(transducer distance deviation) is obtained as a signal deviation ratio, where the maximum signal intensity is plotted along a horizontal axis and the signal deviation ratio along a vertical axis to thereby indicate a degree of damage of an articular cartilage by a location of a plot.

3. The ultrasonograph according to claim 1, wherein an ultrasonic travel-time of the diagnosis object is obtained utilizing signals obtained by changing respective positions of the transmitting ultrasonic transducer or the receiving ultrasonic transducer and a difference between the detected ultrasonic travel-time and the travel-time is obtained based on an acoustic velocity distribution of a numerical model of the diagnosis object repeatedly until the difference converges within an allowable value.

4. The ultrasonograph according to claim 1, wherein the receiving ultrasonic transducer and the transmitting ultrasonic transducer are tilted at an angle in a range of 45 to 85 degrees with respect to an object plane.

5. A diagnostic ultrasonograph comprising:
a probe housing a transmitting and receiving ultrasonic transducer provided at a central location thereof configured to determine a proper orientation angle of the probe, a transmitting ultrasonic transducer provided at a first side of the transmitting and receiving ultrasonic transducer and a receiving ultrasonic transducer provided at a side of the transmitting and receiving ultrasonic transducer opposite to the first side, the transmitting ultrasonic transducer and the receiving ultrasonic transducer being configured to move independently of each other;
a processor configured to obtain an acoustic velocity distribution across a cross-section of a diagnosis object by processing echo signals of the receiving ultrasonic transducer, echo signals of the transmitting and receiving ultrasonic transducer and the distance between the independently movable ultrasonic transducers; and
a display configured to display graphically the acoustic velocity distribution and a signal intensity of the transmitting and receiving ultrasonic transducer.

6. The ultrasonograph according to claim 5, wherein the receiving ultrasonic transducer and the transmitting ultrasonic transducer are tilted an angle in a range of 45 to 85 degrees with respect to an object plane.

* * * * *